United States Patent
Cantu et al.

(10) Patent No.: US 6,466,879 B1
(45) Date of Patent: Oct. 15, 2002

(54) SYSTEMS AND METHODS FOR MONITORING INTRODUCTION OF A PROCESSING FLUID DURING A FLUID PROCESSING PROCEDURE

(75) Inventors: Robert J Cantu, Lake in the Hills; Russel Stinoff, Alrlington Heights, both of IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/615,390

(22) Filed: Jul. 13, 2000

(51) Int. Cl.⁷ .............................................. G06F 17/00
(52) U.S. Cl. ........................ 702/50; 702/173; 702/55; 210/782
(58) Field of Search .............................. 702/50, 45, 46, 702/19, 21, 31, 32, 55, 100, 114, 127, 129, 137, 156, 173, 174, 175, 176–178, 182, 183, 187, 188, FOR 113, FOR 119, FOR 121, FOR 127, FOR 128, FOR 139, FOR 135, FOR 149, FOR 152–FOR 154, FOR 170–FOR 172; 377/19–21; 604/30, 4.01, 5.01, 6.01, 6.05; 435/2; 422/67, 73; 436/10; 700/266, 281–283, 240; 210/645, 647, 782, 739; 494/37; 177/1, 3, 4, 25.19, 25.11–25.13

(56) References Cited

U.S. PATENT DOCUMENTS

| | | | | |
|---|---|---|---|---|
| 4,954,128 A | | 9/1990 | Ford ........................ | 604/6.05 |
| 5,200,090 A | | 4/1993 | Ford et al. .................. | 210/739 |
| 5,370,802 A | | 12/1994 | Brown ....................... | 210/782 |
| 5,676,841 A | | 10/1997 | Brown ....................... | 210/739 |
| 5,693,232 A | * | 12/1997 | Brown et al. ............... | 210/782 |
| 5,980,760 A | * | 11/1999 | Min et al. ................... | 210/782 |
| 6,027,441 A | * | 2/2000 | Cantu et al. ................ | 210/782 |

* cited by examiner

*Primary Examiner*—Hal Wachsman
(74) *Attorney, Agent, or Firm*—Daniel D. Ryan; Bradford R. L. Price; Michael C. Mayo

(57) ABSTRACT

Fluid processing systems and methods make use of a replenishable source containing a volume of a processing fluid that is dispensed during a processing period. A processor serves to sequentially pause and resume the processing period. The processor records weight values of the source at commencement of the processing period; upon pauses in the processing period; and upon resumptions of the processing period. At termination of the processing period, the processor generates a total volume value of processing fluid dispensed from the source during the processing period, which takes into account replenishment of the processing fluid when the processing period is paused. The systems and methods can be integrated into blood processing circuits to monitor the introduction of anticoagulant.

19 Claims, 2 Drawing Sheets

US 6,466,879 B1

SYSTEMS AND METHODS FOR MONITORING INTRODUCTION OF A PROCESSING FLUID DURING A FLUID PROCESSING PROCEDURE

FIELD OF THE INVENTION

The invention generally relates to fluid processing systems and methods. More particularly, the invention relates to blood processing systems and methods.

BACKGROUND OF THE INVENTION

Certain on-line blood collection procedures entail the processing of relatively large volumes of whole blood. This, in turn, requires the introduction of relatively large volumes of anticoagulant to the whole blood during processing period. It is important to accurately monitor the total volume of anticoagulant used during the procedure. This task becomes complicated when the operator is called upon to periodically pause the procedure to replenish the anticoagulant supply.

SUMMARY OF THE INVENTION

The invention provides systems and methods for keeping accurate track of a total fluid volume administered from a fluid source that can be periodically replenished during a fluid processing procedure.

One aspect of the invention provides fluid processing systems and methods that make use of a replenishable source containing a volume of a processing fluid. The systems and methods include a circuit to dispense the processing fluid from the source during a processing period. A weigh sensor is coupled to the source and operates to sense weight of the source. Knowing the density of the processing fluid, the weight translates to volume of processing fluid present in the source.

The systems and methods further include a processor coupled to the weigh sensor. The processor operates in response to commands to sequentially pause and resume the processing period. The processor includes a counting function that operates in a series of processing steps. The processing steps (i) record a current weight value of the source at commencement of the processing period; (ii) register a first subsequent weight value (Wt1) of the source upon pause in the processing period; (iii) register a second subsequent weight value (Wt2) of the source upon resumption of the processing period following the pause; (iv) generate an updated current weight value upon resumption of the processing period by adding to the current weight value the difference between Wt2 and Wt1; (v) register a final weight value of the source at termination of the processing period; and (vi) generate a total volume value of processing fluid dispensed from the source during the processing period, by subtracting the final weight value from the updated weight value. Due to the processing steps followed, the total volume value will take into account replenishment of the processing fluid when the processing period is paused.

Another aspect of the invention integrates the fluid processing systems and methods just described into blood processing systems and methods. According to this aspect of the invention, the processing fluid is introduced into a blood processing circuit. In one embodiment, the blood processing circuit separates blood into component parts. In this embodiment, the processing fluid comprises an anticoagulant solution that is added to the blood during processing.

Features and advantages of the inventions are set forth in the following Description and Drawings, as well as in the appended claims.

DESCRIPTION OF THE PREFERRED EMBODIMENTS

Figure 1:
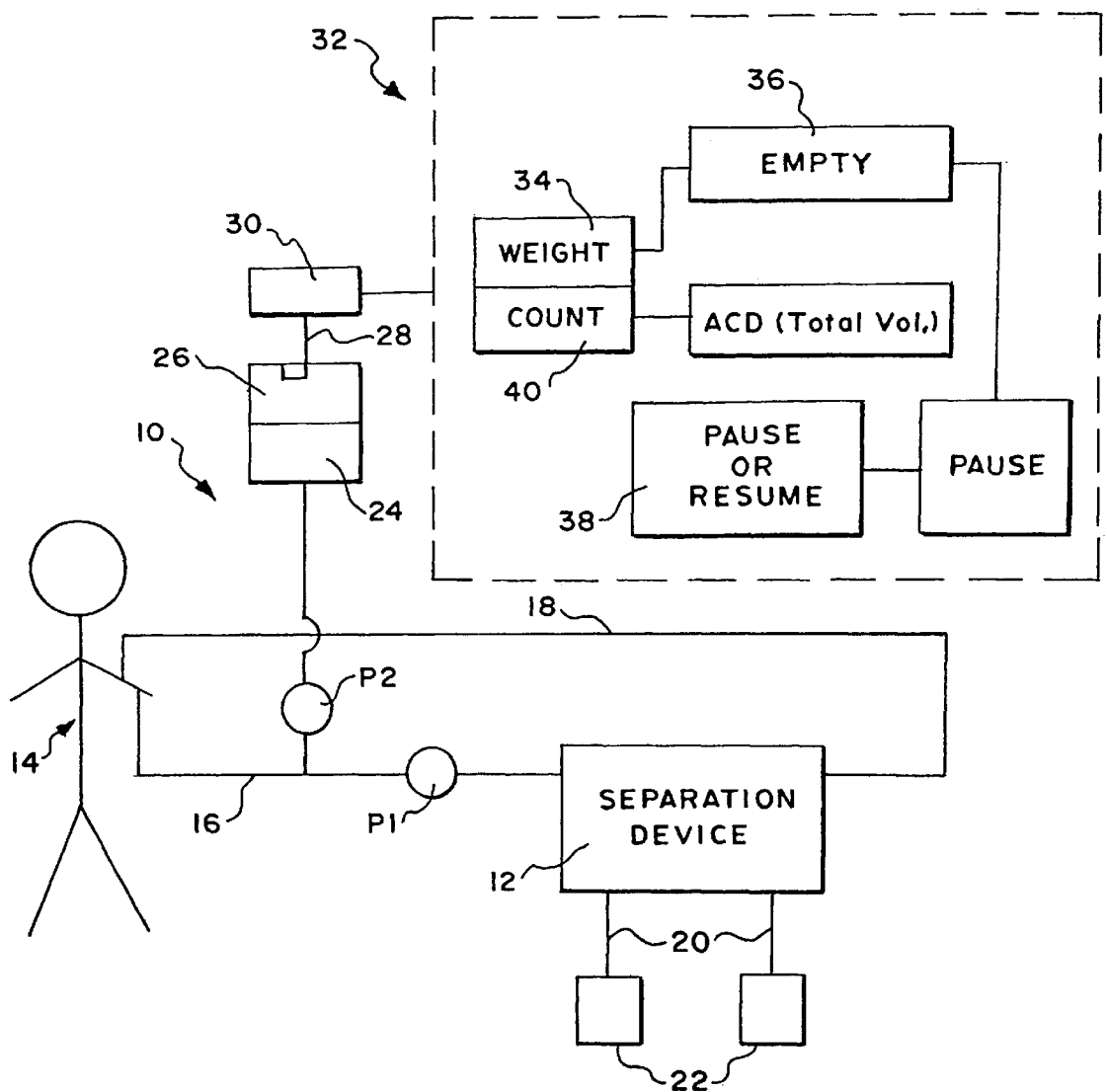
FIG. 1 is a schematic view of a fluid processing system that incorporates feature of the invention.

FIG. 1 shows an extra-corporeal blood processing system 10. The system 10 includes a device 12 in which whole blood drawn from a donor 14 is separated into its principal component parts, i.e., red blood cells, platelets, and plasma. In certain, more specialized procedures, other less numerous component species, such as mononuclear cells, can be harvested using the device 12.

The device 12 can take various forms. In the illustrated embodiment, the device 12 takes the form of a centrifuge.

An inlet line 16 draws whole blood from the donor 14 and conveys it (by operation of an inlet pump P1) into the centrifuge 12 for processing. An outlet line 18 typically returns selected blood components, e.g., red blood cells and at least some of the plasma, to the donor 14 either continuously or in batches. One or more collection lines 20 convey the components targeted for collection to appropriate storage containers 22.

Further details concerning systems and methods for processing blood on-line in this manner, either continuously or in a series of draw and return cycles, are well known and are not material to the invention. Representative systems are disclosed, e.g., in U.S. Pat. No. 5,370,802; U.S. Pat. No. 5,676,841; and U.S. Pat. No. 5,980,760, which are incorporated herein by reference.

Various processing fluids are introduced during a typical blood separation process. For example, saline is typically added to prime and flush the system. Saline can also be introduced as a replacement fluid.

As FIG. 1 show, an anticoagulant solution 24, e.g., acid-citrate-dextrose (ACD), is also metered by a pump P2 from a source 26 into the whole blood inlet line 16 throughout the procedure, to prevent blood coagulation. The source 26 containing the anticoagulant solution 24 is typically a flexible bag, which is typically suspended on a hook 28 near the centrifuge 12.

It is important to account for the volume of anticoagulant solution 24 introduced during a given procedure. For this purpose, a weigh scale 30 monitors the weight of the source bag 26. Knowing the density of the anticoagulant solution 24 (which, for ACD, is approximately 1 g/ml), the weight of the anticoagulant solution 24 can be translated to volume of anticoagulant solution 24. Changes in the sensed weight can thereby be translated into volume of anticoagulant solution 24 delivered.

Relatively large volumes of whole blood are required to be processed during certain blood collection procedures; for example, in the collection of less numerous species of mononuclear cells. During these procedures, the overall volume of anticoagulant solution 24 required to be added can exceed the volume of anticoagulant solution 24 contained in a given source bag 26 (which is typically about 500 ml). In this circumstance, the operator needs to replenish the anticoagulant solution source 26, by pausing the procedure and exchanging an empty or near empty bag 26 with a full bag 26. In this way, the supply of anticoagulant solution 24 is sustained during the procedure. It is desirable to maintain an accurate account of the total volume of anticoagulant solution 24 introduced in this dynamic environment, regardless of how many source bags 26 are used or exchanged during a given procedure.

According to the invention, the system 10 includes a processor 32 coupled to the weigh scale 30. The processor 32 includes a weight function 34 that monitors the weight of the anticoagulant solution source bag 26. The weight function 34 compares the monitored weight to a set threshold weight, and generates an EMPTY source signal 36 when the monitored weight falls below the set threshold (e.g., 100 ml). The EMPTY source signal pauses the blood processing procedure to prompt the operator to replenish the anticoagulant solution bag 26. The operator can also manually pause the procedure when desired for this or another reason, by using an appropriate input device 38 coupled to the processor 32. The operator can manually resume the procedure using the device 38 or another suitable input.

The processor 32 also includes a counting function 40 that accumulates the changes in weight of the one or more anticoagulant solution source bags 26 used during a procedure, to derive the total volume of anticoagulant solution 24 used, designated ACD(Total Vol).

Figure 2:
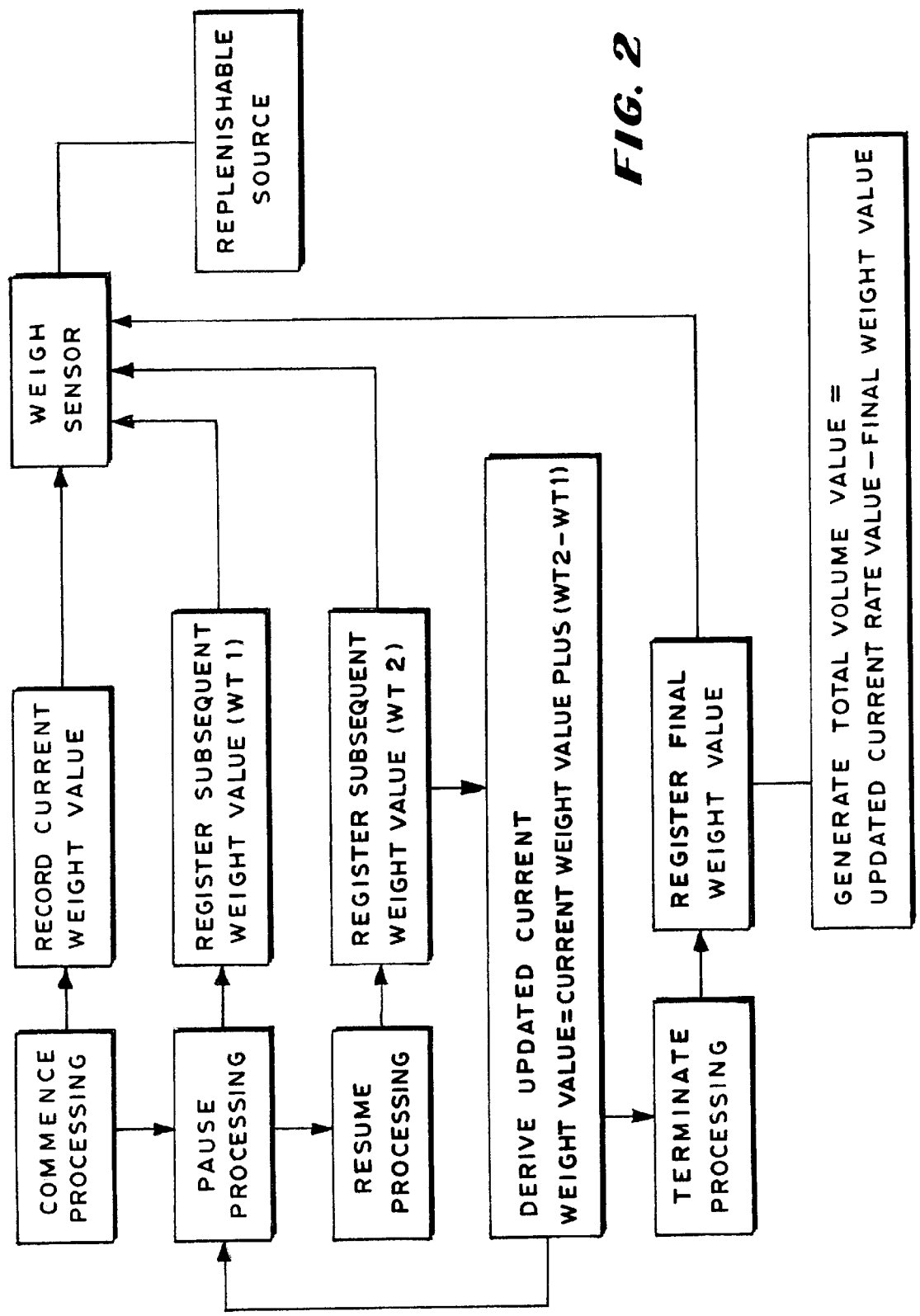
FIG. 2 is a flow chart showing a fluid processing method that incorporates features of the invention.

At the outset of a given blood processing procedure (see also FIG. 2), the weight function 34 registers the weight of the anticoagulant solution 24 source bag 26. The counting function 40 records this value as ACD(Initial). The weight function 34 continues to monitor the weight of the anticoagulant solution source bag 26 and compare it to the EMPTY source threshold.

If the operator manually pauses the procedure (using the device 38), or if the weight function 34 generates an EMPTY source signal 36 to pause the procedure, the counting function 40 registers the current weight of the anticoagulant solution source bag 26 and records this value as ACD(in). When the procedure resumes, the counting function 40 again registers the current weight of the anticoagulant solution source bag 26 and records this value as ACD(out).

Upon resumption of a paused procedure, the a counting function 40 updates ACD(Initial) as follows:

$$ACD(\text{Initial})_{New} = ACD(\text{Initial})\text{Old} + ACD(\text{Diff})$$

where:

$$ACD(\text{Diff}) = ACD(\text{out}) - ACD(\text{in})$$

When the anticoagulant solution source bag 26 is not exchanged during a given pause in the procedure, ACD(Diff) is zero (this is because no anticoagulant solution 24 is introduced when the system 10 is paused, as no additional whole blood is being drawn). However, when the anticoagulant solution source bag 26 is exchanged during a given pause in the procedure, ACD(Diff) will reflect the difference in weight between the previous source bag 26 and the new source bag 26.

The counting function 40 updates ACD(Initial) in this manner each time the procedure is paused, either manually or by generation of the EMPTY source signal 36, and then resumed.

The processor 32 will generate a PROCEDURE WRAP-UP command when the criteria governing the particular blood collection procedure are met (e.g., a targeted volume of whole blood has been processed, or a targeted volume of blood component has been collected). The operator, too, can manually generate a PROCEDURE WRAP-UP command using an appropriate input device. In response to the PROCEDURE WRAP-UP command, the counting function 40 registers the current weight of the anticoagulant solution source bag 26 and records this value as ACD(Final).

The counting function 40 then derives the total volume of anticoagulant solution 24 used—ACD(Total Vol)—as follows:

$$ACD(\text{TotalVol}) = ACD(\text{Initial})_{New} - ACD(\text{Final})$$

where $ACD(\text{Initial})_{New}$ is the most current updated value of ACD(Initial).

EXAMPLE

At the outset of a blood processing procedure, the operator hangs a full anticoagulant solution source bag 26 (e.g., 500 ml) on the hook 28. The weight function 34 registers the weight of the source bag 26 as 500 g (i.e., 500 ml). The counting function 40 records ACD(Initial)=500.

The operator causes a first manual pause of the procedure. The weight function 34 now registers the weight of the source bag 26 as 400 g (i.e., 400 ml), which indicates that 100 ml of anticoagulant solution 24 have been introduced since the beginning of the procedure. The counting function 40 records ACD(in)=400. During this pause, the operator does not exchange the anticoagulant solution source bag 26. When the procedure is resumed, the weight function 34 still registers the weight of the source bag 26 as 400 g (i.e., 400 ml). The counting function 40 records ACD(out)=400, and generates ACD(Diff)=0. The counting function 40 updates $ACD(\text{Initial})_{New}$=500 (i.e., 500 plus 0).

The operator causes a second manual pause of the procedure. The weight function 34 now registers the weight of the source bag 26 as 300 g (i.e., 300 ml), which indicates that an additional 100 ml of anticoagulant solution 24 have been introduced between the first and second pauses. The counting function 40 records ACD(in)=300. Again, during this pause, the operator does not exchange the anticoagulant solution 24 source bag 26. When the procedure is resumed, the weight function 34 still registers the weight of the source bag 26 as 300 g (i.e., 300 ml). The counting function 40 records ACD(out)=300, and generates ACD(Diff)=0. The counting function 40 updates $ACD(\text{Initial})_{New}$=500 (i.e., 500 plus 0).

An EMPTY source signal 36 causes a third pause in the procedure, when the weight function 34 registers the contents of the source bag 26 as being 100 ml, i.e., at the 100 ml threshold. The counting function 40 records ACD(in)= 100, which also indicates that 200 ml of anticoagulant have been introduced between the second and third pauses. In this pause, the operator is prompted to exchange the near empty anticoagulant solution source bag 26, replacing it with a new source bag 26 (containing, e.g., 500 ml of anticoagulant solution 24).

The weight function 34 registers the weight of the new source bag 26 as 500 g (i.e., 500 ml). When the procedure is resumed, the counting function 40 records ACD(out)=500, and generates ACD(Diff)=400. The counting function 40 updates ACD(Initial)New=900 (i.e., 500 plus 400).

In time, the processor 32 will generate a PROCEDURE WRAP-UP command, or the command is otherwise generated by the operator. The weight function 34 registers the weight of the source bag 26 as 250 g (i.e., 250 ml). This indicates that 250 ml of additional anticoagulant solution 24 have been introduced between the third pause and the PROCEDURE WRAP-UP command. The counting function 40 registers the current weight of the anticoagulant solution 24 source bag 26 and records this value as ACD(Final)=250. The counting function 40 then derives ACD(Total Vol)=650 ml (i.e., 900–250).

As the Example demonstrates, the value of ACD(Total Vol) derived in this fashion by the counting function 40 in effect preserves and sums up the incremental volumes of anticoagulant solution 24 introduced between procedure start-up and the first pause (100 ml); between the first pause and the second pause (100 ml); between the second pause and the third pause (200 ml); and between the third pause and the PROCEDURE WRAP-UP command (250 ml). Despite the exchange of the anticoagulant source bag 26 once or several times while processing is paused, the counting function 40 continuously preserves and carries forward all incremental weight changes, which translate to incremental fluid volumes.

The invention has been described in the context of blood processing, because it is well suited for use in this environment. Still, it should be appreciated that use of the invention is not limited to blood processing. The features of the invention can be used in association with any system in which it is desired to track the volume of processing fluid used during a given processing procedure.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

The features of the invention are set forth in the following claims.

We claim:

1. A fluid processing system comprising
a replenishable source containing a volume of a processing fluid having a known density,
a circuit to dispense the processing fluid from the source during a processing period,
a weigh sensor coupled to the source and operating to sense weight of the source that is proportional to volume of processing fluid present in the source, and
a processor coupled to the weigh sensor and operating in response to commands to sequentially pause and resume the processing period, the processor including a counting function that operates in processing steps to (i) record a current weight value of the source at commencement of the processing period; (ii) register a first subsequent weight value (Wt1) of the source upon pause in the processing period; (iii) register a second subsequent weight value (Wt2) of the source upon resumption of the processing period after the pause; (iv) generate an updated current weight value upon resumption of the processing period by adding to the current weight value the difference between Wt2 and Wt1; (v) register a final weight value of the source at termination of the processing period; and (vi) generate a total volume value of processing fluid dispensed from the source during the processing period, which takes into account replenishment of the processing fluid when the processing period is paused, by subtracting the final weight value from the updated current weight value.

2. A system according to claim 1
wherein the processor includes a weigh function to compare a weight value of the source to a set low threshold and generate a pause command when the weight value is at or below the set low threshold.

3. A system according to claim 1
wherein the processor includes an input device to receive pause or resumption commands from an operator.

4. A system according to claim 1
wherein the processor operates to repeat processing steps (ii), (iii), and (iv) to generate an updated current weight value each time the processing period is paused and resumed.

5. A blood processing system comprising
a blood processing circuit including a device operating to separate blood into component parts,
an auxiliary line operating to convey a processing fluid into the blood processing circuit,
a replenishable source coupled to the auxiliary line, the source containing a volume of a processing fluid having a known density,
a weigh sensor coupled to the source and operating to sense weight of the source that is proportional to volume of processing fluid present in the source, and
a processor coupled to the weigh sensor and operating in response to commands to sequentially pause and resume a processing period using the blood processing circuit, the processor including a counting function that operates in processing steps to (i) record a current weight value of the source at commencement of the processing period;(ii) register a first subsequent weight value (Wt1) of the source upon pause in the processing period; (iii) register a second subsequent weight value (Wt2) of the source upon resumption of the processing period after the pause; (iv) generate an updated current weight value upon resumption of the processing period by adding to the current weight value the difference between Wt2 and Wt1; (v) register a final weight value of the source at termination of the processing period; and (vi) generate a total volume value of processing fluid dispensed from the source during the processing period, which takes into account replenishment of the processing fluid when the processing period is paused, by subtracting the final weight value from the updated current weight value.

6. A system according to claim 5
wherein the processing fluid comprises an anticoagulant solution.

7. A system according to claim 5
wherein the processor includes a weigh function to compare a weight value of the source to a set low threshold and generate a pause command when the weight value is at or below the set low threshold.

8. A system according to claim 5
wherein the processor includes an input device to receive pause or resumption commands from an operator.

9. A system according to claim 5
wherein the processor operates to repeat processing steps (ii), (iii), and (iv) to generate an updated current weight value each time the processing period is paused and resumed.

10. A method for monitoring volume of processing fluid introduced into a fluid processing system comprising the steps of
establishing a replenishable source containing a volume of a processing fluid having a known density, dispensing the processing fluid from the source during a processing period, sensing weight of the source that is proportional to volume of processing fluid present in the source, recording a current weight value of the source at commencement of the processing period, registering a first subsequent weight value (Wt1) of the source upon a pause in the processing period, registering a second subsequent weight value (Wt2) of the source upon a resumption of the processing period after the pause, generating an updated current weight value upon resumption of the processing period by adding to the current weight value the difference between Wt2 and Wt1, registering a final weight value of the source at termination of the processing period, and generating a total volume value of processing fluid dispensed from the source during the processing period, which takes into account replenishment of the processing fluid when the processing period is paused, by subtracting the final weight value from the updated current weight value.

11. A method according to claim 10 further including the step of comparing a weight value of the source to a set low threshold and generate a command to pause the processing period when the weight value is at or below the set low threshold to prompt an operator to replenish the processing fluid.

12. A method according to claim 10 further including receiving pause or resumption commands from an operator.

13. A method according to claim 10 including the step of generating an updated current weight value each time the processing period is paused and resumed.

14. A blood processing method comprising the steps of establishing a blood processing circuit, establishing a replenishable source containing a volume of a processing fluid having a known density, dispensing the processing fluid from the source into the blood processing circuit during a processing period, sensing weight of the source that is proportional to volume of processing fluid present in the source, recording a current weight value of the source at commencement of the processing period, registering a first subsequent weight value (Wt1) of the source upon a pause in the processing period, registering a second subsequent weight value (Wt2) of the source upon a resumption of the processing period after the pause, generating an updated current weight value upon resumption of the processing period by adding to the current weight value the difference between Wt2 and Wt1, registering a final weight value of the source at termination of the processing period, and generating a total volume value of processing fluid dispensed from the source during the processing period, which takes into account replenishment of the processing fluid when the processing period is paused, by subtracting the final weight value from the updated current weight value.

15. A method according to claim 14 wherein the blood processing circuit circulates blood from a donor through a blood separation device.

16. A method according to claim 15 wherein the processing fluid comprises an anticoagulant solution that is added to the blood.

17. A method according to claim 14 further including the step of comparing a weight value of the source to a set low threshold and generate a command to pause the processing period when the weight value is at or below the set low threshold to prompt an operator to replenish the processing fluid.

18. A method according to claim 14 further including receiving pause or resumption commands from an operator.

19. A method according to claim 14 including the step of generating an updated current weight value each time the processing period is paused and resumed.

* * * * *